(12) United States Patent
Case et al.

(10) Patent No.: US 11,793,917 B2
(45) Date of Patent: Oct. 24, 2023

(54) HEATED BLOOD PRESSURE CUFF DEVICE, SYSTEM AND METHOD

(71) Applicant: FENWAL INC., Lake Zurich, IL (US)

(72) Inventors: Brian C. Case, Lake Villa, IL (US); Christian Stonig, Ernstbrunn (AT)

(73) Assignee: FENWAL INC., Lake Zurich, IL (US)

( * ) Notice: Subject to any disclaimer, the term of this patent is extended or adjusted under 35 U.S.C. 154(b) by 970 days.

(21) Appl. No.: 16/627,162

(22) PCT Filed: Jun. 29, 2018

(86) PCT No.: PCT/US2018/040368
§ 371 (c)(1),
(2) Date: Dec. 27, 2019

(87) PCT Pub. No.: WO2019/006349
PCT Pub. Date: Jan. 3, 2019

(65) Prior Publication Data
US 2020/0222617 A1    Jul. 16, 2020

Related U.S. Application Data

(60) Provisional application No. 62/527,280, filed on Jun. 30, 2017.

(51) Int. Cl.
*A61B 5/022* (2006.01)
*A61M 1/36* (2006.01)
*A61M 1/34* (2006.01)

(52) U.S. Cl.
CPC ....... *A61M 1/3639* (2013.01); *A61B 5/02233* (2013.01); *A61M 1/3496* (2013.01);
(Continued)

(58) Field of Classification Search
CPC ....... A61B 5/01; A61B 5/02233; A61B 5/026; A61B 5/11; A61B 5/15003;
(Continued)

(56) References Cited

U.S. PATENT DOCUMENTS 4,883,462 A * 11/1989 Williamson ......... A61H 9/0078
601/152
6,026,684 A    2/2000 Calder
(Continued)

FOREIGN PATENT DOCUMENTS

| EP | 0193399 A2 | 9/1986 |
| KR | 101008128 B1 * | 1/2011 |
| WO | 2016087123 A1 | 6/2016 |

OTHER PUBLICATIONS

International Search Report and Written Opinion by the International Search Authority for International Application No. PCT/US2018/040368, dated Sep. 25, 2018 (15 pages).

*Primary Examiner* — Benjamin J Klein
(74) *Attorney, Agent, or Firm* — Cook Alex Ltd.

(57) ABSTRACT

A system for increasing blood flow through a user's limb during a blood collection procedure includes an inflatable cuff that is worn around the user's limb. A pump and a deflation valve are in fluid communication with the inflatable cuff. A heating element and a temperature sensor are attached to the inflatable cuff. The system also includes a motion sensor. A controller is in communication with the pump, the deflation valve, the heating element and the temperature and motion sensors and detects a blood pressure or blood flow of the user, controls inflation and deflation of the inflatable cuff and controls energization of the heating element based on data from the motion sensor and the temperature sensor.

10 Claims, 2 Drawing Sheets

(52) U.S. Cl.
CPC ............... *A61M 2205/3327* (2013.01); *A61M 2205/3334* (2013.01); *A61M 2205/3337* (2013.01); *A61M 2205/3368* (2013.01); *A61M 2205/36* (2013.01); *A61M 2230/30* (2013.01); *A61M 2230/50* (2013.01)

(58) Field of Classification Search
CPC ............ A61B 5/150076; A61B 5/4836; A61H 9/0092; A61H 2201/0103; A61H 2201/0228; A61H 2201/1207; A61H 2201/165; A61H 2201/50; A61H 2201/5082; A61H 2230/25; A61H 2230/30; A61M 1/02; A61M 1/3496; A61M 1/3639; A61M 2205/3327; A61M 2205/3334; A61M 2205/3337; A61M 2205/3368; A61M 2205/36; A61M 2205/3653; A61M 2230/005; A61M 2230/30; A61M 2230/50; A61M 2230/63
See application file for complete search history.

(56) References Cited

U.S. PATENT DOCUMENTS

| | | | | |
|---|---|---|---|---|
| 7,825,356 B2 * | 11/2010 | Hewes | ................... | A61F 7/007 |
| | | | | 219/548 |
| 2009/0234261 A1 * | 9/2009 | Singh | .................. | A61M 1/3655 |
| | | | | 601/152 |
| 2014/0114117 A1 * | 4/2014 | Naghavi | ............ | A61B 5/02233 |
| | | | | 600/16 |
| 2017/0325825 A1 * | 11/2017 | Bybordi | .......... | A61B 5/150748 |
| 2018/0206746 A1 * | 7/2018 | Narasimhan | ......... | A61B 5/0225 |

* cited by examiner

HEATED BLOOD PRESSURE CUFF DEVICE, SYSTEM AND METHOD

CROSS-REFERENCE TO RELATED APPLICATIONS

The present application is the U.S. National Stage of PCT International Patent Application No. PCT/US2018/040368, filed Jun. 29, 2018, which claims the benefit of and priority to U.S. Provisional Application No. 62/527,280, filed Jun. 30, 2017, the contents of which are hereby incorporated by reference.

FIELD OF THE INVENTION

The present disclosure relates generally to blood drawing, collection and treatment devices, systems and methods and, in particular, to a heated blood pressure cuff device, system and method for increasing blood flow during blood drawing, collection and treatment procedures.

BACKGROUND

During apheresis procedures, whole blood is collected from a donor and separated into components, such as plasma, platelets and white blood cells. These components, which are extremely valuable for medical therapies, are removed and collected, and the remaining processed blood is transfused back to the donor. For therapeutics, the targeted cells are removed and replaced with "good" cells, or the targeted cells are removed and treated (filtered or chemically) and then reinfused into the patient.

Poor blood flow from a donor or patient may result in slower collection times for apheresis procedures. Prior art approaches to increasing blood flow include having the donor/patient squeeze a ball or a heat pack. In addition the donor/patient may be covered with a blanket to keep them warm.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a system for increasing blood flow through a user's limb during a blood collection procedure includes an inflatable cuff configured to be worm around the user's limb. A pump and a deflation valve are in fluid communication with the inflatable cuff. A heating element, a motion sensor and a temperature sensor are attached to the inflatable cuff. A controller is in communication with the pump, the deflation valve, the heating element and the temperature and motion sensors. The controller is configured to detect a blood pressure of the user, control inflation and deflation of the inflatable cuff and control energization of the heating element based on data from the motion sensor and the temperature sensor.

In another aspect, a device for increasing blood flow through a user's limb during a blood collection procedure includes an inflatable cuff configured to be worn around the user's limb and connected to a pump and a deflation valve. A heating element is attached to the inflatable cuff and configured to be connected to a source of electrical power. A motion sensor and a temperature sensor are also attached to the inflatable cuff and are configured to be placed in communication with a controller that controls the pump, the deflation valve and the heating element.

In yet another aspect, a method for increasing blood flow through a user's limb during a blood collection or therapeutic procedure includes the steps of positioning the user's limb through an inflatable cuff, detecting a blood pressure of the user, warming the user's limb using a heating element positioned in the inflatable cuff so that blood vessels in the user's limb are dilated, detecting a temperature of the user's arm and controlling energization of the heating element and the inflation of the inflatable cuff based on the detected blood pressure and the detected temperature.

DETAILED DESCRIPTION OF EMBODIMENTS

While embodiments are described below in terms of use in an apheresis procedure, the technology of the disclosure may be used in other types of blood collection or therapeutic procedures. Furthermore, while the embodiments are described in terms of an inflatable cuff that is worn around the user's arm, the cuff may alternatively be worn around other limbs of the user. Furthermore, the terms "user" and "donor" are used interchangeably in the following description.

Figure 1:
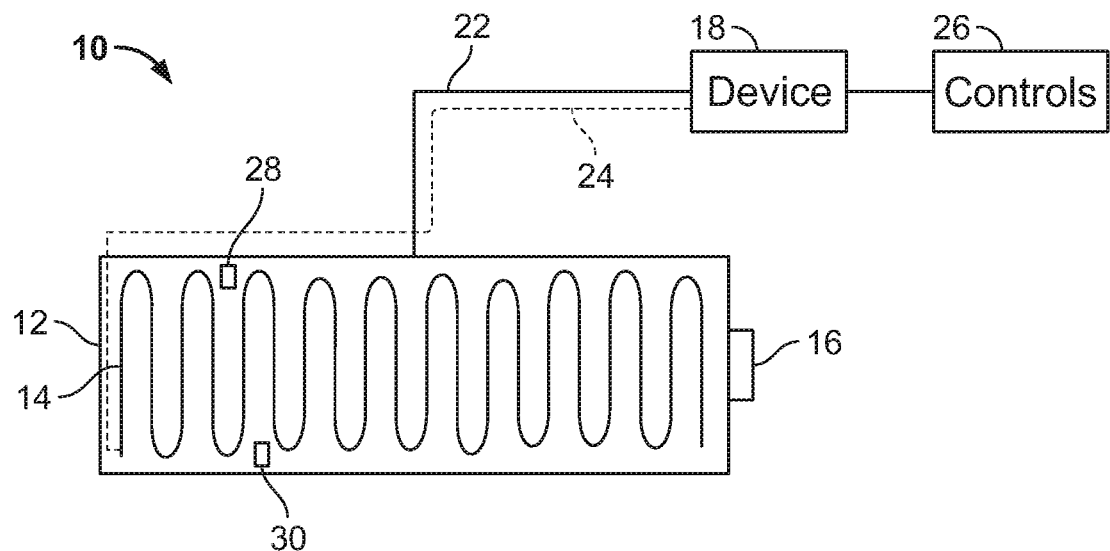
FIG. 1 is a schematic view of a first embodiment of the heated blood pressure cuff system of the disclosure.

An embodiment of the heated inflatable cuff of the disclosure is indicated in general at 10 in FIG. 1. The device includes an inflatable blood pressure cuff 12 within which is positioned one or more heating elements 14. The cuff is sized and dimensioned to be placed around the arm, or other limb, of a user and features a fastening element 16. As an example only the, fastening element 16 may include one portion of a hook and loop material, while the cuff exterior surface may be provided with a mating hook and loop material.

Device 18 includes a pump for inflating the cuff 12, a deflation valve to permit deflation of the cuff and an electrical power regulator to provide electrical power to the heating element 14. The device may be configured to receive power from an external power source or may feature an on-board battery. A pressure tube 22 extends between the pump and deflation valve of the device 18 and the inflatable cuff 12, while an electrical line, illustrated in phantom at 24, is connected between the electrical power regulator of the device 18 and the heating element 14 of the cuff.

A controller 26 is electrically connected to the device 18 as well as a temperature sensor 28 and a motion sensor 30. The controller may be a dedicated component, or the controller of another piece of medical equipment, such as an apheresis device. As explained in greater detail below, the motion sensor 30 may be positioned in the cuff, in an apheresis device or in the tubing of the disposable kit used during the procedure.

The controller 26 includes a microprocessor that is configured to control inflation of the cuff 12 via the pump of the device 18. As is known in the art, the cuff is initially inflated to a level that stops blood flow through the blood vessels of the cuffed arm. The cuff is then deflated by the controller via the deflation valve of the device to a pressure below the systolic pressure so that blood once again flows through the arm.

This results in a vibration in the blood vessel walls that, in embodiments where the motion sensor takes the form of a vibration sensor positioned within the cuff, is detected by the sensor 30 and relayed to the controller 26. The controller 26 includes a microprocessor that converts the data from the motion (vibration) sensor 30 into the blood pressure of the user.

As an alternative to a vibration sensor positioned within the cuff, the motion sensor 30 may be a pressure sensor of an apheresis device. As another alternative, a flow sensor in the tubing of the disposable kit could be used as the motion sensor 30 to measure the blood flow within the vein. In any of these embodiments, the controller 26 detects the blood pressure or blood flow of the user wearing the cuff.

As the user is wearing the inflated cuff, the heating element 14 in the cuff may be energized. The heat provided by the heating element travels through the user's skin and causes the blood vessels in the cuffed arm to dilate. This increases blood flow, and thus reduces the time required for the collection or treatment of blood from the user during the apheresis procedure.

The temperature sensor 28 provides temperature data to the microcontroller of controller 26 so as to provide feedback control of the level of energization of the heating element 14 (via the power regulator of device 18), and thus control of the heat provided by the heating element. The controller 26 is configured to operate the heating element 14 within safe limits based on temperature feedback provided by cuff temperature sensor 28.

The controller preferably is also programmed so that the temperature and motion sensors provide a feedback loop to keep the arm at the best temperature for optimal flow.

Figure 2:
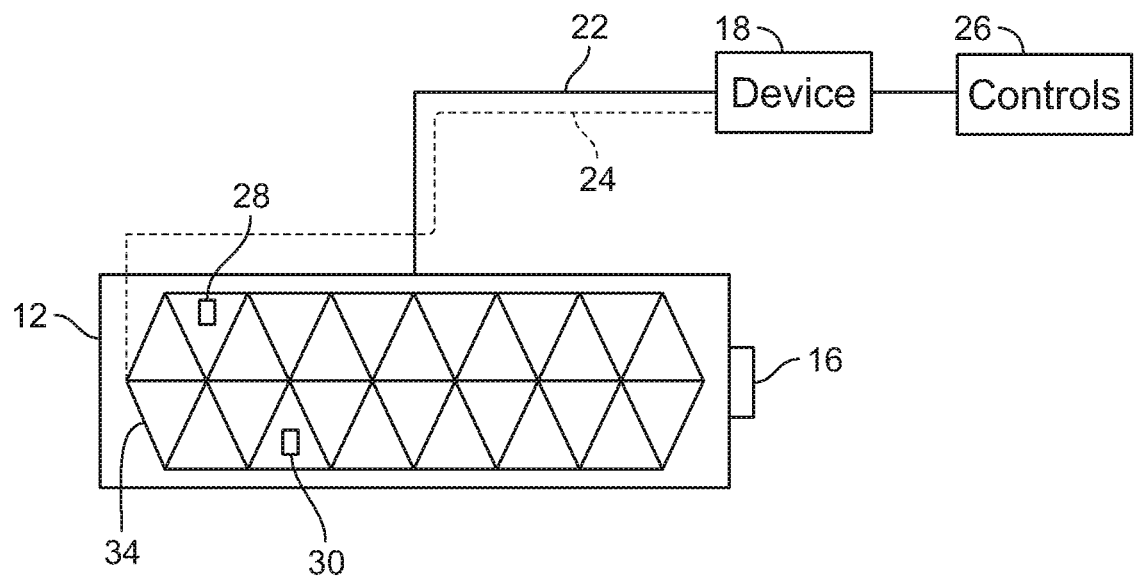
FIG. 2 is a schematic view of a second embodiment of the heated blood pressure cuff system of the disclosure.

As illustrated in FIGS. 1 and 2, the heating elements 14 (FIG. 1) and 34 (FIG. 2) of the may be arranged within the inflatable cuff 12 in a variety of patterns to maximize surface coverage and therefore provide efficient heating of the user's arm. Heating element patterns other than those illustrated in FIGS. 1 and 2 may alternatively be used.

During an apheresis procedure, the controller is configured so that the cuff will inflate during a draw cycle and deflate during a return cycle. The heater element may always be used to some extent in some embodiments.

Figure 3:
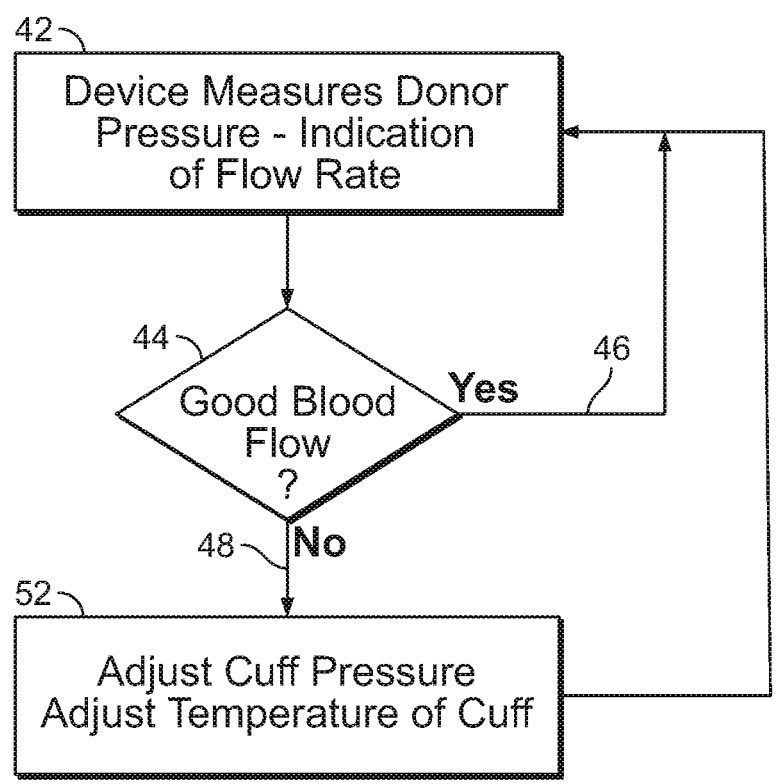
FIG. 3 is a flow chart illustrating operation of the heated blood pressure cuff system in accordance with an embodiment of the disclosure.

A flowchart illustrating an example of the processing performed by controller 26 during an apheresis procedure is illustrated in FIG. 3. A needle is inserted into the user's arm and is placed in fluid communication with blood collection equipment. As indicated at block 42, the cuff 12 of FIGS. 1 and 2 is operated in the manner described above to measure the blood pressure of the user or donor. This provides an indication of the blood flow rate through the blood vessels of the user's arm.

The controller is preferably configured to measure the flow rate/pressure of the vein and adjust the temperature to optimize the blood flow. For example, the controller may continuously (or periodically) check the blood pressure or blood flow via sensor 30, as indicated at 44 in FIG. 3. If the blood flow is good, i.e. is at an acceptable level, the cuff pressure and heating are maintained at their existing levels, as indicated by arrow 46 in FIG. 3. As an example only, normal flow rates for "good" donors are 100-180 ml/minute, with higher flow rates being better. If the blood flow falls below an acceptable level (arrow 48), however, the controller 26 signals the device 18 to adjust the inflation level of the cuff 12 (decreasing it to increase blood flow rate) and the heating level provided by the heating element 14 (increasing it to further dilate the blood vessels), as indicated at block 52 of FIG. 3.

Preferably, the needle stick is right in the crease of the elbow so that the general area around the arm by the needle stick is warmed/heated up.

When used in double-needle procedures, the cuff with the heating element typically would only be on the arm that is used for the draw side. The return side usually never has flow issues (outside of a hematoma) because the system is pumping blood into the arm. During the draw cycle, a "vacuum" is created in the vein, which can collapse it.

It is to be understood that embodiments of the invention include a self-contained system that does all of the control and adjustment of the heater within the cuff and, alternatively, a system where the apheresis device provides the feedback to adjust the heater within the cuff. In the latter embodiment, the cuff assembly requires an electrical connection to the apheresis device.

In addition, embodiments of the system preferably include safety controls on the heater element to minimize damage to the skin, i.e. burns or discomfort, the inflation level of the cuff to not go top high and damage the skin or cut off blood flow and the electrical side to not shock the donor/patient.

While the preferred embodiments of the disclosure have been shown and described, it will be apparent to those skilled in the art that changes and modifications may be made therein without departing from the spirit of the disclosure, the scope of which is defined by the following claims.

What is claimed is:

1. A system for increasing blood flow through a user's limb during a blood collection procedure comprising:
   a. an inflatable cuff configured to be worn around the user's limb;
   b. a pump in fluid communication with the inflatable cuff;
   c. a deflation valve in fluid communication with the inflatable cuff;
   d. a heating element within the inflatable cuff;
   e. a motion sensor;
   f. a temperature sensor attached to the inflatable cuff; and
   g. a controller in communication with the pump, the deflation valve, the heating element and the temperature and motion sensors, said controller configured to detect a blood pressure or blood flow of the user, control inflation and deflation of the inflatable cuff and control energization of the heating element based on data received from a feedback loop provided by the motion sensor and the temperature sensor.

2. The system of claim 1 wherein the pump and the deflation valve are positioned within a device that is controlled by the controller.

3. The system of claim 1 further comprising a power regulator in electrical communication with the heating element and the controller with said controller controlling the power regulator to control energization of the heating element.

4. The system of claim 3 wherein the pump, the deflation valve and the power regulator are positioned within a device that is controlled by the controller.

5. The system of claim 1 wherein the cuff includes a fastening element.

6. A method of increasing blood flow through a user's limb during a blood collection procedure comprising:
   a. positioning the user's limb through an inflatable cuff;
   b. detecting a blood pressure or blood flow of the user using a motion sensor;
   c. warming the user's limb using a heating element positioned in the inflatable cuff so that blood vessels in the user's limb are dilated;
   d. detecting a temperature of the user's limb using a temperature sensor;
   e. providing a feedback loop to a controller with data collected by the motion sensor and temperature sensor; and
   f. controlling energization of the heating element and the inflation of the inflatable cuff based on the detected blood pressure or blood flow and the detected temperature provided by the feedback loop.

7. The method of claim 6 wherein detecting the blood pressure or blood flow of the user using the motion sensor includes inflating the inflatable cuff and deflating the inflatable cuff.

8. The method of claim 6 wherein the user's limb is the user's arm.

9. The method of claim 6 further comprising decreasing power supplied to the heating element when the detected temperature exceeds a predetermined level.

10. The method of claim 6 wherein the blood collection procedure is an apheresis procedure.

* * * * *